US005322057A

United States Patent [19]

Raabe et al.

[11] Patent Number: 5,322,057
[45] Date of Patent: Jun. 21, 1994

[54] INTERMITTENT SIGNAL ACTUATED NEBULIZER SYNCHRONIZED TO OPERATE IN THE EXHALATION PHASE, AND ITS METHOD OF USE

[75] Inventors: Otto G. Raabe, Davis; James I. C. Lee; James C. Hathaway, both of Sacramento, all of Calif.

[73] Assignee: Vortran Medical Technology, Inc., Sacramento, Calif.

[21] Appl. No.: 645,579

[22] Filed: Jan. 24, 1991

Related U.S. Application Data

[63] Continuation-in-part of Ser. No. 585,616, Sep. 20, 1990, Pat. No. 5,080,093, which is a continuation of Ser. No. 270,520, Nov. 19, 1988, abandoned, which is a continuation of Ser. No. 071,202, Jul. 8, 1987, Pat. No. 4,832,012.

[51] Int. Cl.[5] ........ A61M 16/00; A62B 7/04; F16K 31/26; B05B 17/06

[52] U.S. Cl. ........ 128/203.12; 128/204.21; 128/204.26; 128/200.16

[58] Field of Search ........ 128/200.14, 200.21, 128/203.12, 203.13, 203.14, 203.16, 203.17, 203.26, 203.27, 204.17, 204.18, 204.21, 204.26, 204.23, 200.16, 205.24

[56] References Cited

U.S. PATENT DOCUMENTS

| | | | |
|---|---|---|---|
| 2,466,468 | 5/1949 | Neal | 259/108 |
| 2,774,346 | 12/1956 | Halliburton | 128/200.21 |
| 3,211,433 | 10/1965 | Chrostowski et al. | 259/108 |
| 3,345,047 | 10/1967 | Gooden | 128/200.17 |
| 3,362,404 | 9/1968 | Beasley | 128/145.8 |
| 3,379,194 | 4/1968 | Biermann | 128/145.6 |
| 3,610,237 | 10/1971 | Barkalow et al. | 128/145.8 |
| 3,662,751 | 5/1972 | Barkalow et al. | 128/145.8 |
| 3,724,454 | 4/1973 | Brown | 128/200.21 |
| 3,744,764 | 7/1973 | Sedam | 259/44 |
| 3,863,630 | 2/1975 | Cavallo | 128/203.27 |
| 3,990,442 | 11/1976 | Patneau | 128/203.16 |
| 4,106,503 | 8/1978 | Rosenthal et al. | 128/200.18 |
| 4,197,843 | 4/1980 | Bird | 128/200.14 |
| 4,203,434 | 5/1980 | Brooks | 1128/205.23 |
| 4,276,876 | 7/1981 | Hakkinen | 128/200.14 |
| 4,279,250 | 7/1981 | Valenta et al. | 128/200.14 |
| 4,393,013 | 7/1983 | McMenamin | 261/64 B |
| 4,396,015 | 8/1983 | Johnson | 128/200.14 |
| 4,471,773 | 9/1984 | Bunnell et al. | 128/204.21 |
| 4,541,966 | 9/1985 | Smith | 128/200.18 |
| 4,566,451 | 1/1986 | Badewien | 128/200.21 |
| 4,624,251 | 11/1986 | Miller | 128/200.14 |
| 4,635,627 | 1/1987 | Gam | 128/200.14 |
| 4,649,911 | 3/1987 | Knight et al. | 128/200.21 |
| 4,686,974 | 8/1987 | Sato et al. | 128/204.23 |
| 4,747,403 | 5/1988 | Gluck et al. | 128/204.21 |
| 4,750,483 | 6/1988 | Ankartross et al. | 128/203.26 |
| 4,819,629 | 4/1989 | Jonson | 128/203.22 |
| 4,832,014 | 5/1989 | Perkins | 128/203.12 |
| 5,080,093 | 1/1992 | Raabe et al. | 128/203.12 |

FOREIGN PATENT DOCUMENTS

| | | | |
|---|---|---|---|
| 8402656 | 7/1984 | PCT Int'l Appl. | 128/203.12 |

OTHER PUBLICATIONS

"Respiratory Therapy Equipment", Stephen McPherson, 3rd ed., 1985 by C. V. Mosby Co.

*Primary Examiner*—Kimberly L. Asher
*Attorney, Agent, or Firm*—Limbach & Limbach

[57] ABSTRACT

A self-contained, high capacity nebulizer, having automatic mixing and temperature control features is provided, and its method of use. The nebulizer is designed for use in conjunction with mechanical respirators, ventilators, or breathing machines, and for this purpose will use electrical signals generated by or received from the respirator to automatically control and synchronize the nebulizing and mixing functions such that nebulization occurs only during the exhalation phase of the respiratory function to load the gas passageway of the respirator to the patient with a standardized dose of medicinal aerosol. Upon commencement of the inhalation phase, the aerosol in the gas passageway is ventilated into the lungs of the patient to which it is attached.

17 Claims, 2 Drawing Sheets

INTERMITTENT SIGNAL ACTUATED NEBULIZER SYNCHRONIZED TO OPERATE IN THE EXHALATION PHASE, AND ITS METHOD OF USE

This application is a continuation-in-part of copending U.S. patent application Ser. No. 07/585,616, filed on Sep. 20, 1990, now U.S. Pat. No. 5,080,093, which was a continuation of U.S. patent application Ser. No. 270,520, filed on Nov. 14, 1988, now abandoned, which was a continuation of U.S. patent application Ser. No. 07/071,202, filed on Jul. 8, 1987, now U.S. Pat. No. 4,832,012.

TECHNICAL FIELD

The present invention relates to nebulizers for creating medicinal aerosols for inhalation therapy. In particular, the present invention relates to nebulizers used during the exhalation phase of the breathing cycle in conjunction with and without interfering with mechanical breathing machines which are used to ventilate the lungs of patients who cannot breathe unaided.

BACKGROUND ART

The thin membrane of the lungs provides an easily penetrated, convenient and generally safe means for obtaining rapid absorption of medication by the body. This is especially desirable where the lungs themselves are diseased or injured. Such medication or drugs are generally delivered to the lung membrane in the form of a fine mist or aerosol which is breathed into the lungs through the nose or mouth of the patient. A variety of devices, called nebulizers by those skilled in the art, have been developed for converting liquids into fine aerosols for this purpose. The simplest of these devices is the hand-held atomizer which converts a liquid to an aerosol when a bulb is compressed to produce a jet of air which atomizes the medication and propels it out of the atomizer. To be effective, the aerosols need to be provided at high concentrations and with droplet size in the respirable range (mass median aerodynamic diameter less than 3 micrometers).

Nebulizers are particularly useful for initiating and continuing respiratory therapy in conjunction with respirators, mechanical ventilators or breathing machines (hereinafter referred to generically as respirators) used to ventilate the lungs of patients having serious respiratory impairment. While some respirators incorporate nebulizers in their design, many do not. Nebulizers incorporated into the structure of such respirators often suffer from many disadvantages. One such disadvantage is severely limited capacity for medication to be nebulized, requiring frequent interruptions in the therapy as new medication is added to the nebulizer reservoir.

Most, if not all, such nebulizers are incorporated in respirators in which the inhalation and exhalation phases of the breathing cycle are triggered by changes in air pressure caused by the patient himself. Such "demand" respirators are not useful for patients whose respiratory systems are paralyzed and incapable of causing even slight changes in air pressure. These patients are aided by mechanical respirators in which the phases of the breathing cycle are triggered by electrical signals. There is now no effective means for patients on such respirators to receive aerosol treatment.

Thus, the need exists for a nebulizer which can be attached to a mechanical respirator, especially those in which the breathing cycle is controlled by an electrical signal, which has a reservoir capacity sufficient to enable several hours of continuous treatment, which can prevent the settling of suspensions or mixtures without creating nebulization-destroying turbulence.

U.S. Pat. No. 4,832,012 discloses the principal of signal actuated synchronization of nebulization for delivery of aerosolized medicine to patients whose breathing is supported or augmented by a mechanical respiratory. In that reference, nebulization could be effected during inhalation or exhalation, but the primary trust of that reference was to provide aerosols during the inhalation phase of the breathing cycle to mix with the inhalation tidal volume provided by the respirator, and in synchrony with the normal operation of the respiratory. However, it has been found that the addition of volume of gas to mix with the inhalation tidal volume provided by the respirator, may interfere with the normal operation of the respirator in certain operating modes, and the medicinal aerosol is diluted by the portion of gas delivered by the respirator.

SUMMARY OF THE INVENTION

The present invention is based upon the nebulization of medicine during and synchronized with the exhalation portion of each breath of the breathing cycle to fill the airline leading from the nebulizer to the patient with a standardized dose of medicinal aerosols that are delivered to the lung by the force of the flow of breathing gas (oxygen-enriched air) delivered by the respirator during the inhalation portion of the breathing cycle. One advantage of this invention is that more concentrated standardized dose of aerosol is delivered to the patient with the first parcel of gas that enters the lungs for each breath during the inhalation process. In addition, the signal used to actuate the nebulizer may be obtained from the ventilator or from an independently generated signal established by the nebulization system utilizing the readily detected respiratory air line pressure or pressure drop across filter from exhaled gas flow. Also, certain safety monitoring features are incorporated into such a system to detect aerosol clogging of respiratory filters and prevent interference with the normal operation of the respirator.

The nebulization system of the present invention can be attached to or operated with a mechanical respirator utilizing either a breathing cycle electrical signal obtained from the respiratory or an independent electrical signal generated by the nebulizer system which detects and responds to the exhalation initiation of the respirator. Such a synchronized signal actuated nebulizer system is designed to operate during the exhalation phase of the breathing cycle while treating a sick patient and efficiently providing, in the short time available, a medicinal aerosol in the appropriate and desired volume, concentration, and particle size distribution for deposition in the respiratory airways of the lungs. An important feature of such a system is that all of the aerosol is generated quickly (in about 1 second or less) and in a way that does not interfere with the control system of the respirator. The nebulizer system has a reservoir of capacity sufficient to enable several hours of continuous treatment and with provision to prevent the settling of suspensions or mixtures without creating nebulization-destroying turbulence, and provides a precisely measured volume of medicinal aerosol generated during patient exhalation in a manner to reach the patient at the precise moment when inhalation begins.

In one embodiment, the present invention provides a nebulizer for use with mechanical respirators which use electrical signals to control the breathing cycle. The nebulizer of this embodiment uses the existing electrical signals from the mechanical respirator to synchronize aerosol generation to fill the gas passageway from the respirator to the patient during the exhalation cycle. Upon the initiation of the inhalation cycle, the aerosol is delivered from the gas passageway to the patient. Nebulization is obtained in this embodiment using the premixed oxygen-enriched air provided at high pressure to the respirator. Automatic temperature regulation and stirring of the liquid medication is optionally provided to preclude concentration change, separation or settling of the medication. Finally, a large volume reservoir is provided to eliminate the need for refilling during lengthy treatment protocols.

DETAILED DESCRIPTION OF THE INVENTION

Figure 1:
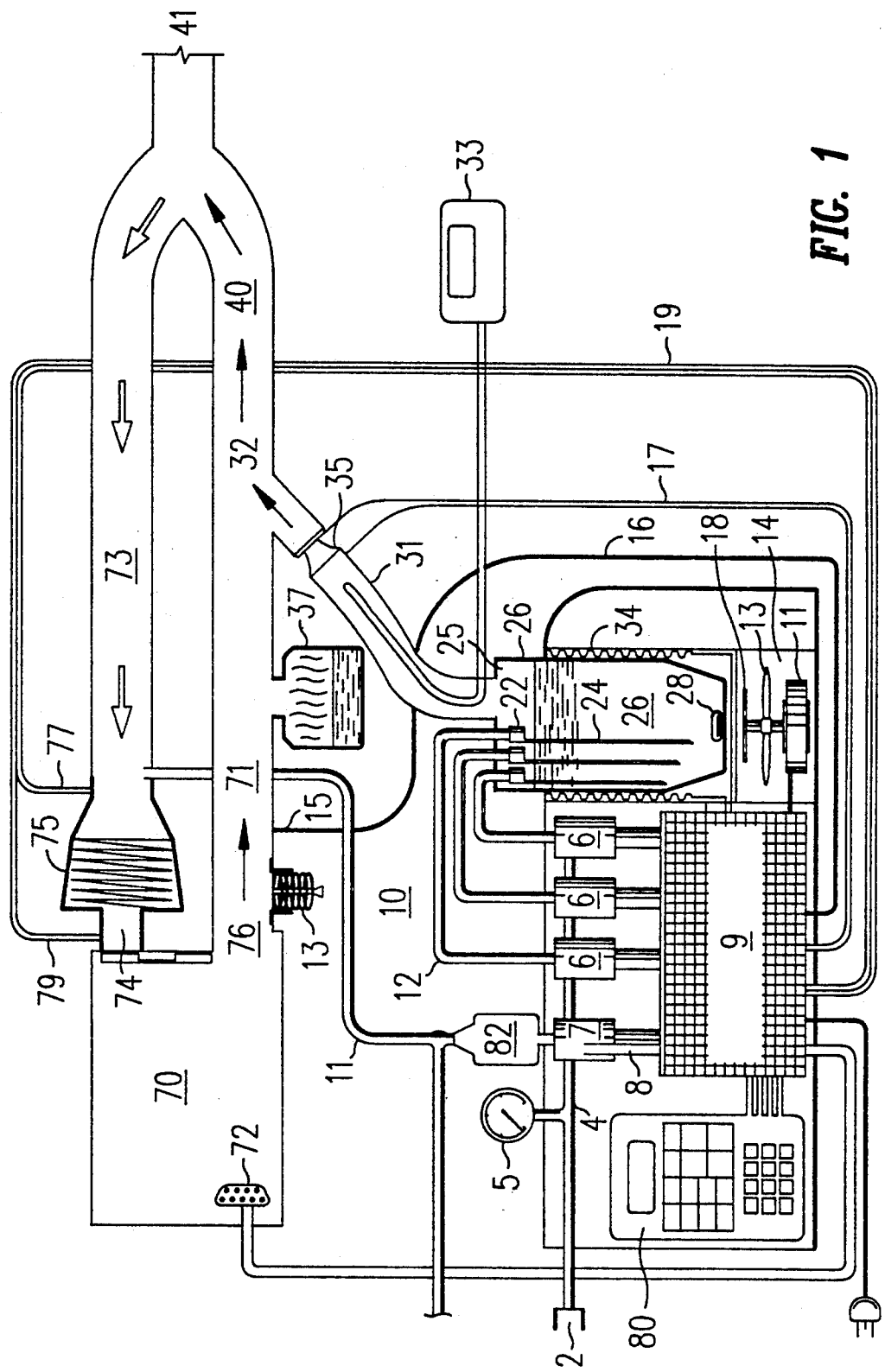
FIG. 1 is a schematic side view of a nebulizer of the present invention operationally attached to a mechanical respirator.

FIG. 1 shows a nebulizer apparatus 10 of the present invention operably connected to a mechanical respirator 70. The nebulizer apparatus 10 comprises, in a housing, compressed gas inlet 2, at one end of a compressed gas conduit 4, adapted to be connected to a compressed gas source at pressure indicated by gauge 5. Preferably this compressed gas source is the same source which is furnishing oxygen-enriched air to the respirator 70, and provides compressed air or oxygen mixture to the nebulizer ranging up to about 50 psig.

Compressed gas conduit 4 is connected at the other end to a first electrically operated nebulizer valve 7, and a plurality of second electrically operated nebulizer valves 6, all of which are substantially similar. Examples of such valves which have been found useful include the Honeywell Skinner K4M ultraminiature 4-way solenoid operated pneumatic valve and Numatics HS series 2-way solenoid operated valves. Three valves 6 are shown in FIG. 1.

Nebulizer valves 6 and 7 are connected by a plurality of electrical lead wires 8 to a microprocessor 9 and are controlled by the microprocessor 9. The microprocessor 9 receives the signals from a signal source 72 on the respirator 70 which controls the inhalation/exhalation phase of the breathing cycle. The microprocessor 9 controls the valves 6 and 7 to provide for a safe and effective operation. Examples of signal source 72 include a respirator solenoid, such as a solenoid actuated inhalation valve, an external electronic monitoring system, or an electronic interface attached to a signal generator on respirator 70, such as an interface connected to a logic circuit in the respirator.

Figure 2:
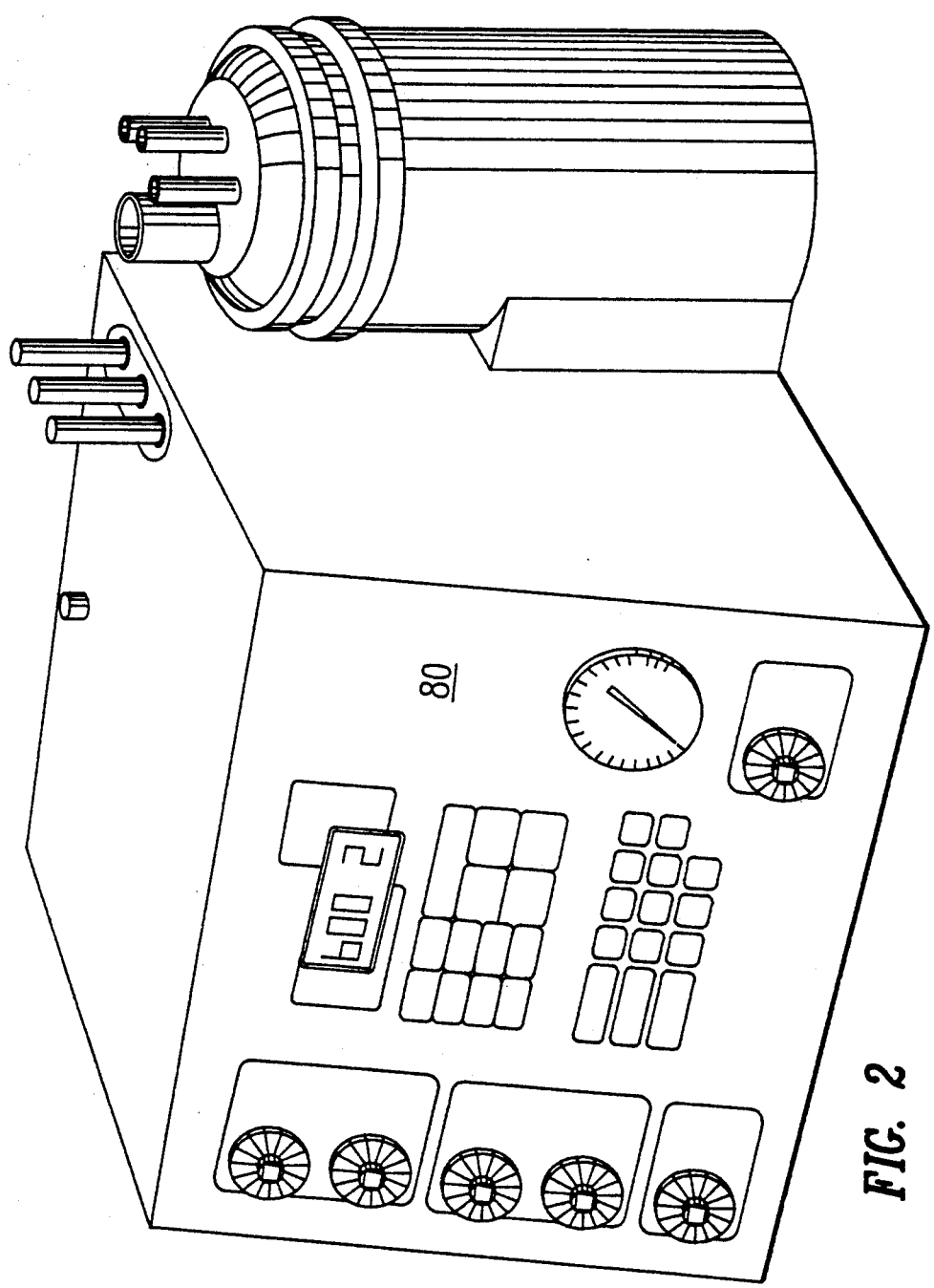
FIG. 2 is a perspective view of the intermittent signal actuated system of the present invention.

A control unit 80, whose control panel is shown in FIG. 2, is connected to the microprocessor 9. The control unit 80 controls the functions of the nebulizing apparatus 10 of the present invention.

Each of the nebulizer valves 6 connects the compressed gas source 4 to nebulizer conduits 12 leading to aerosol nozzles 22. Each nebulizer valve 6 switches between two positions as electrical on/off signals are received. In the first position, during the exhalation phase of the respirator 70 when the electric signal is "on", a passageway is opened between compressed gas conduit 4 and nebulizer conduits 12 and remain open until the desired aerosol volume has generated or until the inhalation phase is initiated by the respiratory 70 as controlled by microprocessor 9. In the second position, when the electric signal is "off", the nebulizer conduits 12 are sealed off.

Nebulizer conduits 12 are attached at their other ends to aerosol nozzles 22, which include liquid feed tubes 24 extending into reservoir 26. Reservoir 26 includes magnetic stirring bar 28 which is located in the bottom of the reservoir. The liquid medicine contained in reservoir 26 is preferably kept at constant temperature by a reservoir heater or cooler 34.

A chamber 14 houses an AC motor 11 which rotates a cooling fan 13 and a magnet 18. The rotation of the magnet 18 causes the stir bar 28 to rotate to prevent sedimentation or separation of medicinal constituents.

The liquid medicine in the reservoir 26 is drawn via the liquid feed tubes 24 and is converted by the aerosol nozzles 22 into an aerosol having droplets with a mass median aerodynamic diameter less than about 3 micron. The aerosol is generated into the air space 25 above the reservoir 26. The aerosol generated in the air space 25 enters into an aerosol tube 31.

The temperature of the aerosol in the aerosol tube 31 is controlled by a temperature controller 33. In one embodiment, the temperature controller is simply an electric heater having a control unit. Within the aerosol tube 31 is also a neb-flow sensor 35. The neb-flow sensor 35 detects the amount of aerosol being delivered through the aerosol tube 31. The output of the neb-flow sensor 35 is supplied as a signal to the microprocessor 9 via neb-flow sensor pressure/vacuum lines 17.

The respirator 70 has an inhalation tube 71 and an exhalation tube 73. The inhalation tube 71 fluidically connects the respirator 70 to a patient and during the inhalation phase, breathing gas is supplied from the respirator 70 along the inhalation tube 71 into the respiratory tract of the patient. The aerosol tube 31 connects the air space 25 above the liquid 26 to the inhalation tube 71 at a nebulizer input 30. In addition, a pop-off valve 13 is also located in the inhalation tube 71. The function of the pop-off valve 13 is to relieve any pressure which is generated to dangerous levels within the inhalation tube 71. It functions purely as an emergency safety valve. Finally, an airway pressure sensor 15 is also positioned in the inhalation tube 71. The airway pressure sensor 15 generates a signal which is also supplied to the microprocessor 9 via airway pressure monitoring line 16. A humidifier 37 whose output is water vapor mixed with the breathing gas is also connected to the inhalation tube 71.

The exhalation tube 73 fluidically connects the patient to the respirator 70. Located within the exhalation tube 73 is an exhalation filter 75. Upstream from the exhalation filter 75, i.e., between the exhalation filter 75 and the patient is an upstream filter pressure sensor 77. Downstream from the exhalation filter 75, i.e., between the exhalation filter 75 and the ventilator 70 is a downstream filter pressure sensor 79. The upstream filter pressure sensor 77 and the downstream filter pressure sensor 79 each provide a signal which is supplied to the microprocessor 9.

The solenoid 7 is also connected to receive gas from the gas conduit 4 and is adapted to supply gas to a decay flow line 11 to the exhalation tube 73, upstream from the upstream filter pressure sensor 77. Thus, the solenoid 7, when activated, provides a stream of compressed gas which is supplied into the exhalation tube 73, between the patient and the upstream filter pressure sensor 77. The function of the decay solenoid 7 is also controlled by the microprocessor 9.

The operation of the nebulizer apparatus 10 of the present invention will be understood as follows. The practitioner first determines the amount of volume per breath of the standardized dose of aerosol which is to be generated by the apparatus 10 of the present invention which is to be supplied to the inhalation tube 71. The amount is entered on the control unit 80. The microprocessor 9 receives the signal and based upon its knowledge of the gas pressure from the compressed gas conduit 4, and the cross-sectional area of each of nebulizing nozzles 22, the microprocessor 9 calculates the amount of time which the solenoids 6 would have to be activated in order to introduce the desired amount of aerosol into the inhalation tube 71. Alternatively, the signal from the neb-flow sensor 35 is used by the microprocessor 9 to turn off the nebulizer solenoids 6 when the desired charging volume has been generated.

When the mechanical respirator 70 begins the exhalation phase of the respiratory cycle, electrical signal 72 supplies the signal to the microprocessor 9. (As will be discussed hereinafter, a number of other signals are supplied to the microprocessor 9 to indicate the beginning of the exhalation cycle. These additional signals are used in the event the ventilator 70 cannot provide the electrical signal source 72 or is used as a safety backup to the electrical signal source 72.) When the mechanical respirator 70 begins the exhalation phase, the inhalation port 76 is closed. The exhalation port 74 is opened, opening the exhalation tube 73.

After the electrical signal source 72 generates the signal indicating the beginning of the exhalation phase, the microprocessor 9 activates the solenoids 6 to the three nebulizing nozzles 24. Thus, after the commencement of the exhalation phase, and after the detection of the electrical signal, maximum generation of the aerosol from the apparatus 10 commences and continues until the standardized volume or dose of aerosol has been generated. Compressed gas flows through the compressed gas conduit 4 into the three nebulizer conduits 12 and into the nozzles 22, which draw liquid via liquid feed tubes 24 from the liquid reservoir 26. The aerosol is then generated and is supplied into the air space 25 above the reservoir 26. The aerosol generated in the air space 25 then enters into the aerosol tube 31 where the temperature thereof is controlled by the temperature controller 33. The aerosol then leaves the aerosol tube 31 and enters into the inhalation tube 71 through port 30. Generation of the standardized dose of aerosol fills the charging volume space 40 between the nebulizer input port 32 and the patient 41 in the inhalation tube 71. Any excessive aerosol will enter the exhalation tube 73 and return to the respirator 70.

During the exhalation phase, the pressure in the inhalation tube 71 is monitored by the airway pressure sensor 15 and is supplied to the microprocessor 9. This provides a safety signal to the microprocessor 9 to shut off the function of the aerosolization in the event pressure within the inhalation tube 71 builds to an excessive level or if inhalation begins. In addition, a mechanical safety pop-off valve 13 is provided wherein in the event the pressure in the inhalation tube 71 exceeds the pressure regulation of the pop-off valve 13, the valve 13 would automatically open relieving the pressure in the inhalation tube 71.

During the exhalation cycle, the respirator 70 continuously monitors the pressure on the exhalation tube 73. In order to provide for a smooth decay flow of gas entering into the exhalation tube 73 from the patient, and thereby simulating smooth exhalation reduction from the patient, the solenoid 7 is activated during the exhalation cycle. When the solenoid 7 is activated, the gas from the compressed gas conduit 4 fills a fixed volume chamber 82. The fixed volume chamber 82 has a calibrated orifice which is connected to the decay flow line 11 and is supplied to the exhalation tube 73. During the time period in which the aerosol is being generated, the fixed volume chamber 82 is filled with breathing gas to a predetermined pressure. At the end of the charging period, the compressed gas from the gas conduit 4 is turned off. The gas from the fixed volume chamber 82 is then allowed to flow in a decay manner into the exhalation tube through the orifice connecting the chamber 82 to the decay flow line 11. When the pressure in the fixed chamber 82 gradually reduces, the flow entering the decay flow line 11 simulates a natural first order decay.

Synchronous with the beginning of the exhalation cycle, the three nebulizing nozzles 22 are turned on simultaneously or one at a time to produce the desired charging volume during a portion of the exhalation period to allow the respirator 70 to maintain and/or support the patient's spontaneous breathing effort without interference from the charging flow.

When the respirator 70 begins the inhalation phase of the respiratory cycle, the electrical signal source 72 switches to an "off" position. In the "off" position, the respirator inhalation port 76 opens; the respirator exhalation port 74 is closed.

The solenoid valves 6 are controlled by microprocessor 9 when first, the desired standardized dose is reached (usually only takes portion of the exhalation phase), or secondly when microprocessor 9 detects the electrical signal source 72 turn to an "off" position. In the first priority, the solenoids 6 can be turned off one at a time. In the second case, the solenoids 6 are turned off immediately to allow respirator 70 to begin the inhalation phase.

The gradual turning off of the plurality of solenoids 6 generates a gradual pressure reduction and flow shaping that prevents spurious triggering of the respiratory ventilator 70 caused by rapid flow changes. Because the aerosol generated by the apparatus 10 of the present invention fills the inhalation tube 71 between the nebulizer input 30 and the patient with the desired standardized volume or aerosol dose, when the ventilator 70 begins the inhalation phase and pushes the gas in the inhalation tube 71 into the respiratory tract of the patient, the aerosol in the charging volume space 40 would be the first gas pushed into the lungs of the patient. Thus, the medicine produced by the aerosol would be first delivered to the patient during the inhalation cycle.

The advantage of the apparatus 10 and method of the present invention is that generating the aerosol and introducing it into the charging volume space 40 during the exhalation phase means the aerosol is pre-charged in the inhalation tube. Further, the amount of aerosol in the charging volume space 40 can be metered or controlled by the microprocessor 9. In addition, the introduction of aerosol during the exhalation phase does not perturb the pressure of the gas from the respirator 70 delivered during the inhalation phase.

As previously discussed, the source of electrical signal 72 may not be provided by all ventilators 70. The upstream filter sensor 77 and the downstream filter sensor 79 each provides a signal via the exhalation filter sensor pressure/vacuum lines 19, the difference of which indicates the commencement of the exhalation phase. Thus, upon the immediate commencement of the exhalation phase, a pressure differential would be detected between the upstream filter sensor 77 and the downstream filter sensor 79, respectively. This pressure differential, supplied as a signal to the microprocessor 9, would indicate to the microprocessor 9 that the exhalation cycle has commenced. This signal can be used by microprocessor 9 to begin nebulization when no respirator electrical signal is available. Alternatively, the airway pressure sensor 15 supplies a signal to the microprocessor 9 indicating the beginning of the exhalation and also the beginning of the inhalation for control of the nebulization by microprocessor 9 when no respirator electrical signal is available.

In addition, there are many safety considerations with the apparatus 10 of the present invention. With the upstream and downstream filter sensor 77 and 79 respectively having an exhalation filter 75 therebetween, the condition of the exhalation filter 75 can be continuously checked. As the apparatus 10 of the present invention is continuously used, and as the filter 75 becomes increasingly clogged, the pressure differential between the upstream filter sensor 77 and the downstream filter sensor 79 would increase. Alternatively, the loading/clogging of the exhalation filter can be detected using the airway pressure sensor 15 which supplies a signal to microprocessor 9 via line 16. This is because airway pressure during nebulization is a function of the resistance of the exhalation filter. The filter loading/clogging can be detected by the microprocessor 9 and can be signaled on the control unit 80 as an alarm that the exhalation filter 75 needs to be examined and/or changed.

As previously discussed, the airway pressure sensor 15 provides an independent airway pressure measurement upstream to exhalation filter to monitor the patients safety. Finally, the control unit 80 can control the apparatus 10 to cause it to pause its operation. This provides an independent check on the respirator system 70. The control unit shown in FIG. 2 provides for setting of charging volume, respirator selection (for different commercial respirators), heater temperature, nebulizer hold option, alarm test option, alarm reset, and alarm silence. Further, the control unit displays respirator selection, charging volume, alarm, warning, and caution, indication of exhalation filter loading, patient peak inspiratory pressure, heater temperature and nozzle gas pressure. Signals from the neb-flow sensor 35 are used to alarm if either inadequate charging volume is generated or if the nebulizer nozzle 24 malfunction in the "on" position. The microprocessor 9 provides yet additional safe and effective operation for the apparatus 10 of the present invention. In the preferred embodiment, the microprocessor 9 is an Intel 8751 available from Intel Corporation. A copy of the program, written in the assembly language, for execution by the microprocessor 9 is attached as Exhibit A.

What is claimed is:

1. A nebulizer in combination with an external electrical signal source, said nebulizer comprising:
    a housing containing a reservoir for holding a liquid to be nebulized and an air space above the reservoir for holding aerosol;
    a plurality of nebulizer nozzles each having a conduit for permitting the flow of gas therethrough;
    a plurality of gas controlling means, one of said gas controlling means positioned in each said nozzle conduit and controlling the flow of gas therethrough;
    a gas flow means for directing compressed gas from a compressed gas source to each of said plurality of gas controlling means for each of said nebulizer nozzles;
    means for attaching said housing to said external electrical signal source, said external electrical signal source generating a first electrical signal during said exhalation phase;
    central control means, responsive to said first electrical signal for controlling the plurality of gas controlling means to introduce said aerosol into a gas flow passageway, connected to the patient, said aerosol filling said gas flow passageway during a portion or all of said exhalation phase, means for monitoring the amount of aerosol introduced into gas flow passageway, said central control means also controlling the plurality of gas controlling means to terminate the flow of said aerosol through each said conduit nozzle into said gas flow passageway one at a time, after a predetermined volume of said aerosol has been monitored as entering into said gas flow passageway.

2. The nebulizer of claim 1 further comprising:
    means for generating a decreasing flow of gas; and
    means for directing said decreasing flow of gas into said mechanical respirator.

3. The nebulizer of claim 1 wherein said central control means activates said plurality of gas controlling means simultaneously to open the flow of gas therethrough, in response to said first electrical signal.

4. The nebulizer of claim 3 wherein said central control means activates said plurality of gas controlling means simultaneously to close the flow of gas therethrough, in response to said second electrical signal.

5. The nebulizer of claim 1, wherein said external electrical signal source comprises a mechanical respirator having an inhalation phase, an exhalation phase, and a gas flow passageway to a patient.

6. A method of operating a nebulizer having means for generating an aerosol; means for supplying said aerosol to a mechanical respirator having an inhalation phase, an exhalation phase and a gas passageway to a patient, and an external electrical signal source generating a first electrical signal during said exhalation phase, said method further comprising:
    generating said aerosol;
    introducing said aerosol into said gas passageway during a portion or all of said exhalation phase;
    monitoring the amount of aerosol introduced into said gas passageway; and
    gradually ceasing the introduction of said aerosol into said gas passageway after a predetermined amount of aerosol has been introduced.

7. The method of claim 6 wherein said introducing step further comprises:

opening a valve, in response to said first signal, to introduce said aerosol from said nebulizer to said gas passageway.

8. The method of claim 6 wherein said generating step further comprises:
entraining a liquid into a source of compressed gas to generate said aerosol, in response to said first electrical signal.

9. The method of claim 6 wherein said external electrical signal source generates a second electrical signal during said inhalation phase.

10. The method of claim 9 further comprising:
ceasing the generation of said aerosol in response to said second electrical signal.

11. A nebulizing attachment in combination with a respirator means having an inhalation phase for inhaling and an exhalation phase for exhaling, a first tubing means connecting said respirator means with a patient wherein during said inhalation phase said respirator means is fluidically connected to the patient through said first tubing means for introducing gas in said first tubing means into the respirator tract of the patient, a second tubing means connecting said respirator means with the patient wherein during said exhalation phase said respirator means is fluidically connected to the patient through said second tubing means for receiving exhaled gas from the patient into said respirator means; said nebulizing attachment comprising:
a filter pressure sensor for detecting the pressure differential in said second tubing means, and for generating a filter pressure signal in response thereto;
an airway pressure sensor for detecting the pressure in said first tubing means, and for generating an airway pressure signal in response thereto;
means for receiving said filter pressure signal and said airway pressure signal and for generating a first electrical signal synchronized with the commencement of said exhalation phase;
means for generating an aerosol;
aerosol connecting means for connecting said generating means to said first tubing means;
means for introducing said aerosol into said first tubing means in response to and synchronized with said first electrical signal;
means for monitoring the amount of aerosol introduced into said gas passageway; and
means for gradually terminating the introduction of said aerosol into said first tubing means after a predetermined volume of aerosol is introduced into said first tubing means.

12. A respirator having an inhalation phase for inhaling and an exhalation phase for exhaling for use with a patient, comprising:
a first tubing means for connection to the patient;
a second tubing means for connection to the patient;
means for introducing gas in said first tubing means into the respiratory tract of the patient during said inhalation phase and for receiving exhaled gas from the patient during said exhalation phase;
a filter pressure sensor for detecting the pressure differential in said second tubing means, and for generating a filter pressure signal in response thereto;
an airway pressure sensor for detecting the pressure in said first tubing means, and for generating an airway pressure signal in response thereto;
means for receiving said filter pressure signal and said airway pressure signal and for generating a first electrical signal synchronized with the commencement of said exhalation phase;
means for generating an aerosol;
aerosol connecting means for connecting said generating means to said first tubing means;
means for introducing said aerosol into said first tubing means in response to and synchronized with said first electrical signal;
means for monitoring the amount of aerosol introduced into said gas passageway; and
means for gradually terminating the introduction of said aerosol into said first tubing means after a predetermined volume of aerosol is introduced into said first tubing means.

13. A method of operating a nebulizer having means for generating an aerosol; means for supplying said aerosol to a mechanical respirator having an inhalation phase, an exhalation phase, a first gas passageway to a patient, and a second gas passageway from the patient, and an external electrical signal source generating a first electrical signal during said exhalation phase, said method further comprising:
generating said aerosol;
introducing said aerosol into said first gas passageway during a portion or all of said exhalation phase;
generating a decreasing flow of volume of gas;
preventing spurious triggering of said mechanical respirator by directing said decreasing flow of volume of gas into said second gas passageway during a portion or all of said exhalation phase;
monitoring the amount of aerosol introduced into said first gas passageway; and
gradually ceasing the introduction of said aerosol into said first gas passageway after a predetermined amount of aerosol has been introduced.

14. The method of claim 13 wherein said introducing step further comprises:
opening a valve, in response to said first electrical signal, to introduce said aerosol from said nebulizer to said first gas passageway.

15. The method of claim 13 wherein said generating step further comprises:
entraining a liquid into a source of compressed gas to generate said aerosol in response to said first electrical signal.

16. The method of claim 13 wherein said external electrical signal source generates a second electrical signal during said inhalation phase.

17. The method of claim 16 further comprising:
ceasing the generation of said aerosol in response to said second electrical signal.

* * * * *